United States Patent [19]
Evans

[11] Patent Number: 5,522,787
[45] Date of Patent: Jun. 4, 1996

[54] MALE SEXUAL AID

[75] Inventor: Henry P. Evans, Chagrin Falls, Ohio

[73] Assignee: Gregory Charles Robinson, Chagrin Falls, Ohio

[21] Appl. No.: 187,194

[22] Filed: Jan. 25, 1994

[51] Int. Cl.⁶ ........................................................ A61F 5/00
[52] U.S. Cl. .................................................. 600/39; 602/61
[58] Field of Search ........................ 600/38–41; 602/5–6, 602/46, 52, 54, 57, 61

[56] References Cited

U.S. PATENT DOCUMENTS

| 844,798 | 2/1907 | Hawley . | |
|---|---|---|---|
| 3,131,691 | 5/1964 | Scott . | |
| 3,401,687 | 9/1968 | Hood .................................. | 600/39 |
| 3,939,827 | 2/1976 | Brunstetter .......................... | 600/39 |
| 4,498,466 | 2/1985 | Pomeranz . | |
| 4,564,006 | 1/1986 | Pomeranz . | |
| 4,733,659 | 3/1988 | Edenbaum et al. ................. | 602/54 |
| 4,899,737 | 2/1990 | Lazarian . | |
| 5,360,390 | 11/1994 | Maanum ............................. | 600/39 |

Primary Examiner—Angela D. Sykes
Assistant Examiner—John P. Lacyk
Attorney, Agent, or Firm—Pearne, Gordon, McCoy & Granger

[57] ABSTRACT

A splint-type sexual aid for a body member, such as a penis, is shown. A soft, elastic support is provided with a semi-rigid stiffener. The support is wrapped around the member and adhered thereto with a pressure sensitive adhesive on the support. A condom is applied over the member and sexual aid. The support is disposable and can be cut to size prior to use.

10 Claims, 1 Drawing Sheet

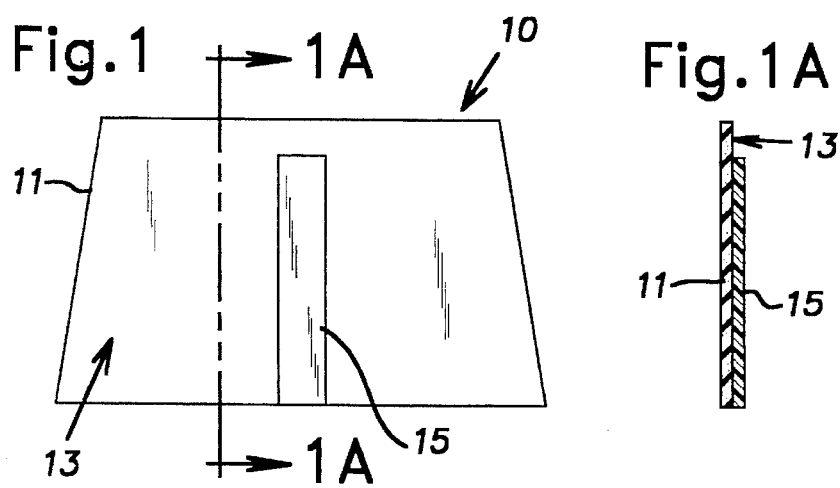
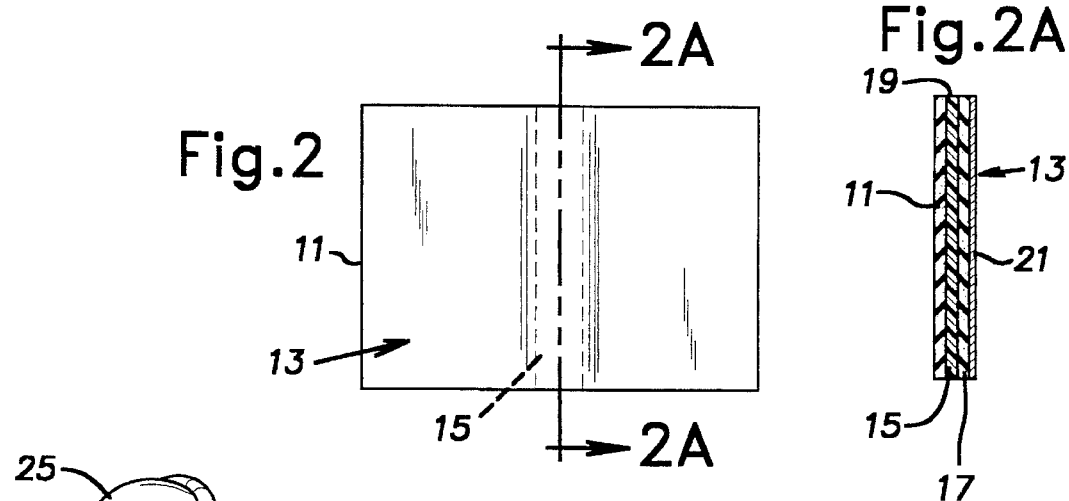
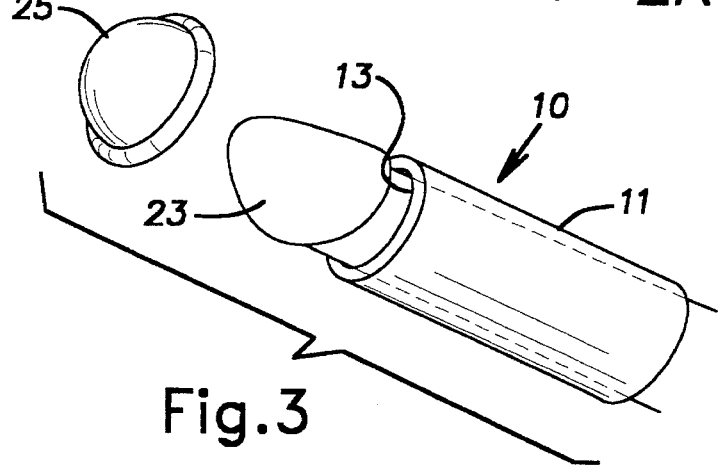
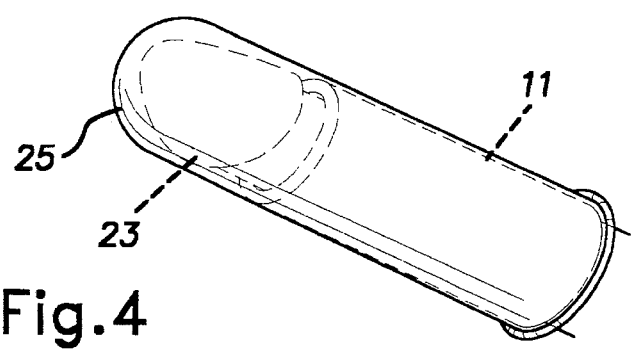

MALE SEXUAL AID

BACKGROUND OF THE INVENTION

1. Field of the Invention

This invention relates generally to the field of sexual appliances and specifically to a male splint.

2. Description of the Related Art

Male impotence is a common problem for which many solutions have been proposed. Among these solutions are mechanical devices applied around a flaccid penis to simulate an erection. Commonly, splints or other rigid members are used to support the penis.

Examples of such splint type devices are shown in U.S. Pat. Nos. 844,798 to Hawley, 3,131,691 to Scott, and 4,899,737 to Lazarian. U.S. Pat. Nos. 4,498,466 and 4,564,006 both to Pomeranz show chambers containing a rheopexic material which hardens to form a support. The devices shown in each of these references are preformed into a generally cylindrical shape and are hereby incorporated by reference.

It would be desirable to have an improved male sexual aid for supporting a penis to be used for sexual intercourse. The support must be easy to apply while ensuring that it does not slip off or become disassembled during use. Most importantly the support should be comfortable. If it is not comfortable, the purpose of the invention is defeated.

SUMMARY OF THE INVENTION

The present invention provides a male sexual aid which includes a generally a flexible, generally planar support adapted to be wrapped around a generally cylindrical human body member, such as a penis. A pressure sensitive adhesive is applied on an inner face of the support so as to adhere the support to the member when the support is wrapped around the member. A semi-rigid splint can be adhered the inner face to provide additional support. A second support, having a shape generally conforming to the first, can be adhered to the first to sandwich the splint therebetween and so that the splint does not directly contact the member. A condom is placed over the support. The adhesive ensures that the aid remains in place without slipping.

The sexual aid is applied by removing a backing from the support, stretching the penis, wrapping the support around the member, and a condom is applied over the member and support. The adhesive adheres the support to the member, so as to leave an end of the member uncovered by the support. The support can be cut to desired dimensions prior to removing the backing.

The sexual aid of the present invention is simple to manufacture and is easily stored and shipped in a compact package. It can easily be adapted to a desired size. In addition, inexpensive materials are used for its manufacture so that it is disposable.

BRIEF DESCRIPTION OF THE DRAWINGS

FIG. 1 shows a plan view of a sexual aid according to the invention;

FIG. 1A shows a sectional view of the sexual aid of FIG. 1 taken from 1A—1A;

FIG. 2 shows a plan view of a sexual aid according to another embodiment of the invention;

FIG. 2A shows a sectional view of the sexual aid of FIG. 2 taken from 2A—2A;

FIG. 3 shows the sexual aid of FIG. 1 as applied to a penis, prior to applying a condom; and FIG. 4 shows the sexual aid of FIG. 3 with the condom applied.

DESCRIPTION OF THE PREFERRED EMBODIMENTS

Referring to FIGS. 1 and 1A, a sexual aid 10 includes a support 11 having a generally trapezoidal shape. The support 11 is made of a soft, but elastic or resilient material, such as cellular polyurethane or foam rubber. The material of the support 11 should be flexible enough to allow the support to be formed into a generally cylindrical shape. In such a cylindrical shape, the support should provide some resistance against bending on a longitudinal axis of the cylinder.

A pressure sensitive adhesive 13, such as an acrylic adhesive, is applied on a face of the support 11. A stiffener 15 is adhered to the support 11 by the adhesive 13. The stiffener 15 is preferably an elongated bar of a semi-rigid material, such as Buna N, with a durometer hardness of about 65. The stiffener should be elastic and should resist bending so as to provide additional stiffness to the support 11. The length of the stiffener 15 should substantially correspond to the height of the support 11, but the stiffener may be slightly shorter. A removable backing (not shown in FIG. 1), such as glossy or waxed paper, is provided over the adhesive 13 to protect the adhesive during storage and transport. 600 Series PVC Foam from Foam Seal, Cleveland, Ohio, has been used for the support and may be purchased with a suitable adhesive and backing applied to the foam.

Referring to FIGS. 2 and 2A, an alternative embodiment of the sexual aid includes the support 11, pressure sensitive adhesive 13, and the stiffener 15. In addition, a second support 17 substantially identical with the first support 11 is adhered to the first support 11 by an adhesive 19. The adhesive 19 may be of the same type as the pressure sensitive adhesive 13 or of another suitable type. The stiffener 15 is sandwiched between the two supports 11, 17. A removable backing 21, such as a waxed paper, is applied over the pressure sensitive adhesive 13 for protection.

As shown in FIG. 2, the supports 11, 17 can have a rectangular shape. This facilitates manufacture because long sheets of support material can be fed from opposing rolls having a line of stiffener material fed therebetween. Adhesive is applied to the supports and backing can be rolled onto one face. The entire assembly is then pressed together. The supports can be cut to size or provided on rolls. Individual supports can be provided in compact, relatively flat packages.

Referring to FIG. 3, the sexual aid 10 is applied over a generally cylindrical member, such as a penis 23. If necessary, the support 11 can be cut to desired dimensions with scissors, for example. Then, the backing is peeled from the support and the penis is slightly stretched to a comfortable length. The sexual aid is wrapped around the penis with the stiffener 15 and the adhesive 13 facing toward the penis. The long dimension of stiffener is generally parallel with a longitudinal axis of the member. The support is pressed firmly onto the penis so that the pressure sensitive adhesive adheres the support thereto so as to prevent slipping.

To provide a smoother, more comfortable outer contour, a condom 25 is applied over the sexual aid, as shown in FIG. 4. Subsequent steps are well known in the art and need not be further described here.

The sexual aid described herein acts as a splint and accordingly may be used as such for members other than a penis. For example, the sexual aid may be used to partially immobilize a finger. In such a case, the supports can be cut to correspond to a desired circumference as well as a desired length. The support may also be cut as necessary to provide access to a wound while providing support for the wounded member. The support may be cut with a taper or a bulge to conform to a tapered or bulging member. The shape is limited only by the size of the stock material and the skill of the cutter.

As will be apparent to one skilled in the art, any of many readily available materials may be used for the various parts of the sexual aid. For example, when the support is used on a sprained digit the support need not provide the same level of resilience or "sponginess" as when it is used on a penis since comfort is not as critical. Where two support members are used, as shown in FIG. 2, one support may be more rigid while the other is more resilient. The stiffener may be made of a strip of metal or plastic, for example, so that it is thin while providing the necessary stiffness. The primary considerations include providing sufficient support for the member while maintaining an adequate level of comfort. All of the materials used should be sterile and non-toxic to external body parts.

The present disclosure describes several embodiments of the invention, however, the invention is not limited to these embodiments. Other variations are contemplated to be within the spirit and scope of the invention and appended claims.

What is claimed is:

1. A male sexual aid for supporting a flexible generally cylindrical body member, comprising:
   a flexible, generally planar support adapted to be wrapped around the generally cylindrical body member;
   a pressure sensitive adhesive separate from but applied on an inner face of the support so as to adhere the support to the member around which it is wrapped, thereby supporting the member in a generally cylindrical shape so as to resist bending of the member; and
   a semi-rigid stiffener disposed on a face of the support so as to be generally parallel with an axis of the member when the support is wrapped around the member, so as to further resist bending of the member.

2. A male sexual aid according to claim 1, wherein the stiffener has a generally rectangular shape.

3. A male-sexual aid according to claim 1, further comprising a second flexible support having a shape generally conforming to the first flexible support and adhered to the first flexible support so as to sandwich the stiffener therebetween, the second flexible support providing additional support for the member.

4. A male sexual aid according to claim 1, wherein the flexible support has a generally quadrangular shape.

5. A male sexual aid according to claim 1, wherein the flexible support has a generally symmetrical, trapezoidal shape.

6. A male sexual aid according to claim 1, wherein the flexible support comprises a cellular polyurethane.

7. A male sexual aid according to claim 1, further comprising a condom applied over the support after the support is wrapped around the member, so as to hold the support in place and provide a generally smooth outer surface.

8. A method of applying a male sexual aid, comprising the steps of:
   cutting a flexible, generally planar support from a larger piece of support material;
   removing a backing from the flexible, generally planar support adapted to be wrapped around a generally cylindrical body member and having a pressure sensitive adhesive applied on an inner face of the support so as to adhere the support to the member, said backing protecting the adhesive;
   wrapping the support around the member, so as to leave an end of the member uncovered by the support, the adhesive adhering the support to the member, so as to support the member in a generally cylindrical shape and resist bending of the member; and
   applying a condom over the member and support so as to hold the support in place and provide a smooth outer surface.

9. A method according to claim 8, further comprising the step of stretching the member before wrapping the support.

10. A method according to claim 8, further comprising the step of cutting the support to desired dimensions before removing the backing.

* * * * *